United States Patent [19]
Andersen

[11] Patent Number: 5,456,263
[45] Date of Patent: Oct. 10, 1995

[54] DETECTOR FOR DETECTING HEART DEPOLARIZATIONS

[75] Inventor: Hans Andersen, Hässelby, Sweden

[73] Assignee: Pacesetter AB, Solna, Sweden

[21] Appl. No.: 338,088

[22] Filed: Nov. 9, 1994

[30] Foreign Application Priority Data

Nov. 24, 1993 [SE] Sweden ................................. 9303891

[51] Int. Cl.$^6$ .............................. A61N 1/362; A61B 5/04
[52] U.S. Cl. ........................ 128/708; 607/26; 128/672; 128/696
[58] Field of Search .................................. 128/672, 696, 128/699, 703, 704, 708; 607/26

[56] References Cited

U.S. PATENT DOCUMENTS

| | | | |
|---|---|---|---|
| 3,939,824 | 2/1976 | Arneson et al. | 128/672 |
| 4,417,306 | 11/1983 | Citron et al. | |
| 5,024,221 | 6/1991 | Morgan . | |
| 5,265,603 | 11/1993 | Hudrlik . | |
| 5,271,393 | 12/1993 | Callaghan | 607/26 |

OTHER PUBLICATIONS

Patent Abstracts of Japan, vol. 14, No. 435 (C–760), Application No. 63–323904.
Patent Abstracts of Japan, vol. 15, No. 100 (C–813), Application No. 64–133193.

Primary Examiner—Lee S. Cohen
Assistant Examiner—Stephen Huang
Attorney, Agent, or Firm—Hill, Steaman & Simpson

[57] ABSTRACT

A compact, power-sparing detector for detecting heart polarizations is described. The detector has a first operational amplifier which uses sensed heart signals from a heart as an input signal. By means of feedback coupling via a second operational amplifier, a resistor and a capacitor, the system strives to achieve a minimum voltage gradient across the input terminals of the first operational amplifier. When an electrical signal with a signal slope corresponding to a heart depolarization arrives at the input terminal of the first operational amplifier, the second operational amplifier is no longer able to damp the input signal, and a peak output signal is sent from the first operational amplifier to each of a first comparator and a second comparator, respectively. The comparators produce an output signal as long as the output signal from the first operational amplifier is maximal, and the output signal from the comparators is integrated in a time integrator in order to determine the duration of the output signals. If a sufficient duration elapses, a detection signal is generated at the output terminal.

10 Claims, 2 Drawing Sheets

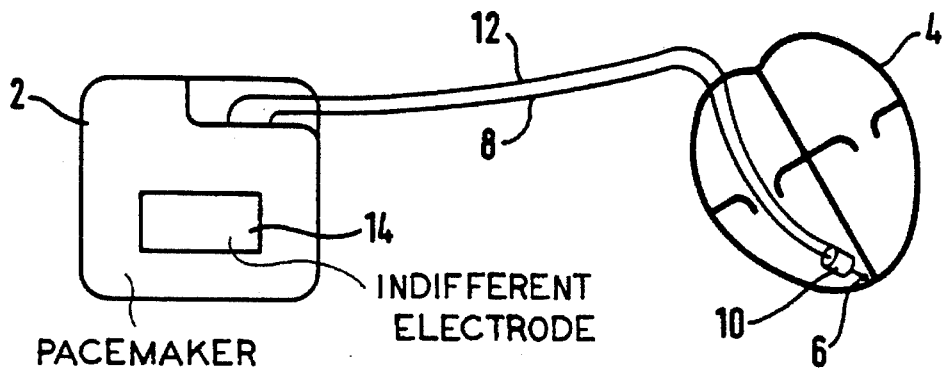
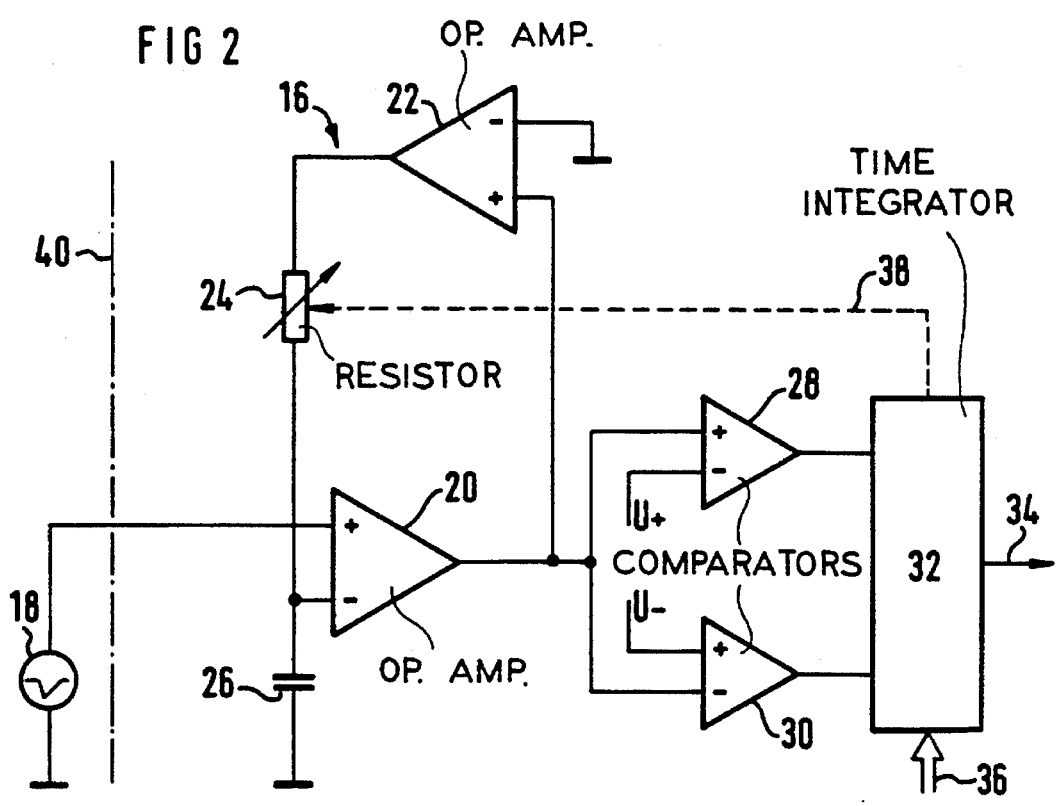

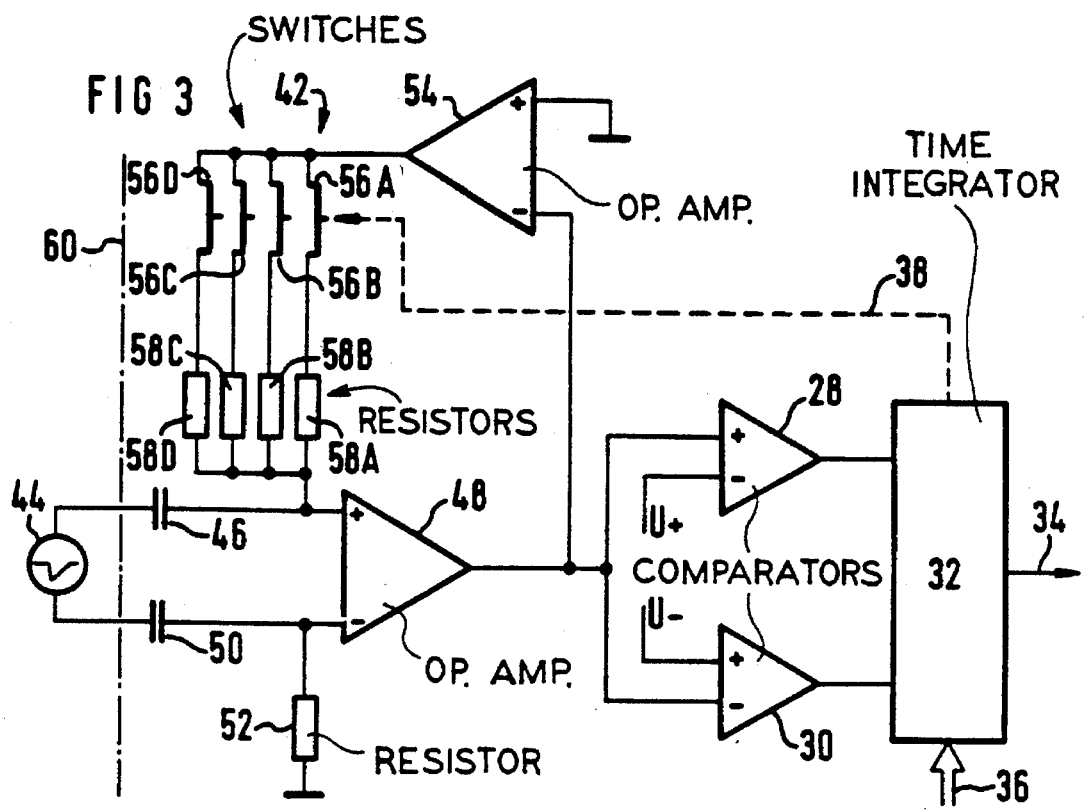
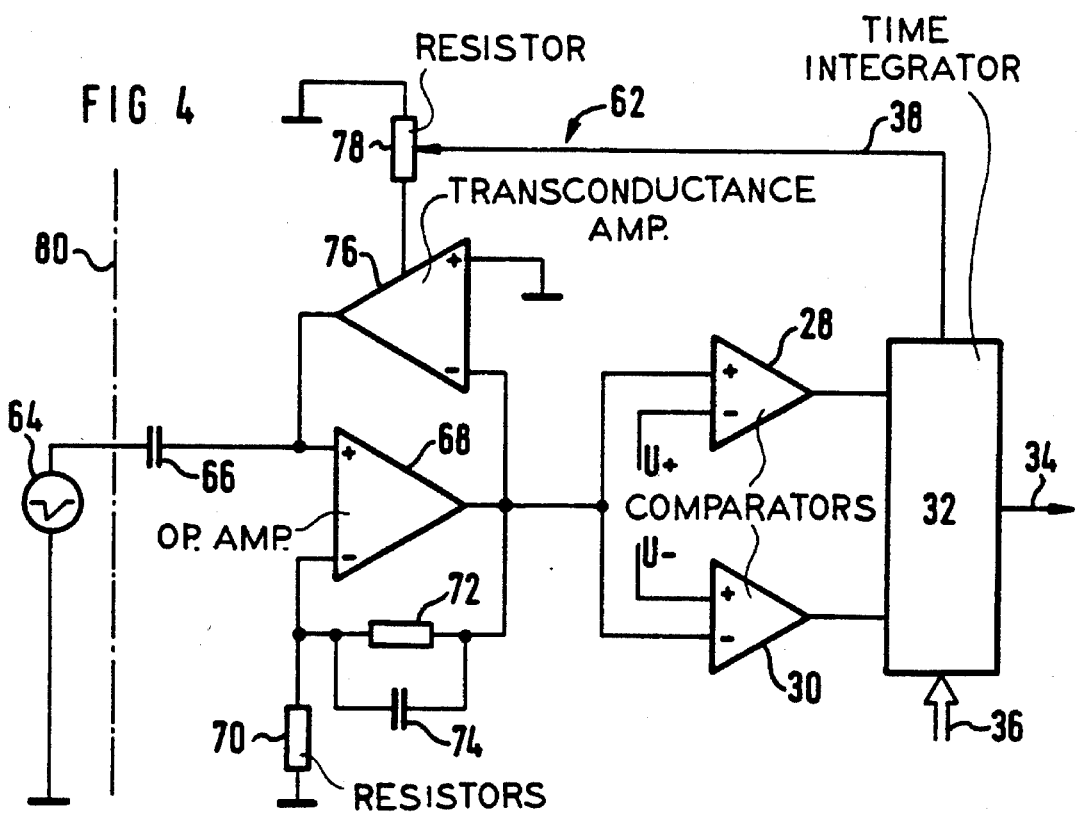

DETECTOR FOR DETECTING HEART DEPOLARIZATIONS

BACKGROUND OF THE INVENTION

1. Field of the Invention

The present invention relates to a detector for detecting heart depolarizations by sensing electrical signals from a heart.

2. Description of the Prior Art

Reliable detection of spontaneous heart depolarizations is important in the monitoring and treatment of a heart. One known way of detecting heart depolarizations is to record the heart's electrical signals (ECG signals) and to analyze same. In particular, such signals are analyzed to identify the QRS complex, appearing when the ventricles depolarize, which displays very distinctive, fast intrinsic deflection, i.e., rapid changes in the signal. Detection can be identified by analysis of the signal's change (derivative) and duration. This is described in e.g., U.S. Pat. No. 4,417,306.

Power consumption is a problem when detectors are implemented in implantable pacemakers and defibrillators (ICD). An implantable apparatus only has access to the limited amount of energy stored in its battery, and a detector, which should be active most of the time in order to detect heart depolarizations, must not consume too much power.

Space is another problem with implantable devices. Pacemaker and defibrillator designs are becoming increasingly smaller. So components used in such devices must occupy as little space as possible.

SUMMARY OF THE INVENTION

One object of the invention is to achieve a detector which solves the aforesaid problems.

Another object of the invention is to achieve a detector in which detection conditions can be changed to improve the detector's usefulness with different types of heart signals.

One such detector is achieved in accordance with the invention in which includes an operational amplifier with an input terminal for receiving the heart's electrical signals sensed by an electrode system, and a regulatory circuit, which is feedback coupled across the operational amplifier in order to minimize the voltage gradient between the operational amplifier's input terminals as long as the electrical signals have a flatter slope than a regulated signal slope. An electrical signal with a steeper signal slope than the regulated signal slope causes a peak positive or negative output signal from the operational amplifier, depending on whether the signal slope is positive or negative. A time-sensing circuit sets an interval during which at least the positive or the negative output signal from the operational amplifier is maximal, and a heart polarization is assumed to occur, and is thus detected, when the predetermined interval exceeds a predetermined detection time.

Components are utilized which can advantageously be arrayed on a microchip, and thus occupy very little space. The components are also very power-sparing. As long as the slope of the voltage signal at the detector's input terminal is not sufficiently steep, the regulatory circuit will continuously adjust the voltage gradient between the operational amplifier's input terminals to make it zero, in principle. When a signal with a sufficiently steep slope arrives at the detector's input terminal, i.e., a signal slope characteristic of the QRS complex, the regulatory circuit is no longer able to maintain a zero voltage gradient across the operational amplifier's input terminals, and the operational amplifier is therefore fully driven, i.e., produces a maximal swing as an output signal. Depending on whether a positive slope or a negative slope is sensed, the output signal will be maximally positive or maximally negative. To ensure that interference signals, such as interference spikes with a steep slope, are not interpreted as detected heart depolarizations, timing of an interval is begun during which the operational amplifier continues to supply a peak output signal, i.e., as long as the slope of the input signal is steeper than the predetermined signal slope. If the timed interval has a duration which exceeds a predetermined detection time, the signal is interpreted as being caused by a depolarization in the heart.

In an embodiment of the detector in accordance with the invention the interval timing circuit includes a first comparator, for comparing the output signal from the operational amplifier to a positive limit voltage, and which supplies an output signal as long as the output signal from the operational amplifier is higher than the positive limit voltage, and a second comparator, for comparing the output signal from the operational amplifier to a negative limit voltage, and which supplies an output signal as long as the negative output signal from the operational amplifier is lower than the negative limit voltage.

The QRS complex is dominated by the R wave which, depending on the electrode system employed, exhibits at least one characteristic signal component. For example, in unipolar electrode systems, the QRS complex has a steep negative slope. In bipolar electrode systems, the QRS complex can consist of both a steep positive slope and a steep negative slope (the negative slope sometimes appears first and sometimes the positive slope, depending on the direction of propagation of the depolarization wave). It is therefore advantageous if the detector can detect both the positive and negative slopes, individually, as well as both slopes consecutively.

For this purpose, the interval timing circuit of the detector preferably further includes a time integrator for determining the duration of the output signal from the first comparator and the second comparator respectively and for comparing this duration to he predetermined detection time.

Time integration of the output signal from the comparator supplies the period of time in which the arriving heart signal satisfies the condition for steepness, i.e., the derivative is sufficiently large. The time integrator can be realized in a number of ways, e.g., by charging capacitors, using an operational amplifier, etc. Satisfaction of the condition for duration can be checked if the time-integrated signal is compared to the detection time. When the latter elapses, the sensed electrical signal is approved as a heart depolarization. Otherwise it is rejected. Alternatively, time integration could be performed throughout the time in which there is an output signal from the comparator and then be compared to the detection time. Duration could naturally be determined even with the aid of some other type of timer.

An additional advantage of time integration throughout the time in which the comparator supplies an output signal is achieved in one embodiment wherein the detector is devised so the signal slope is programmable, and the time integrator is connected to the regulatory circuit in order to vary the signal slope according to the duration of the detected heart signal, thereby regulating the detector's sensitivity.

In a corresponding manner, the detector can be devised so the predetermined detection time in the time integrator is programmable and the time integrator automatically varies the detection time according to the predetermined duration of the output signal from the respective comparator in order to achieve a predetermined detection margin. In principle, the detection margin, i.e., the difference between the duration and detection time, expressed as a percent of the duration, designates the risk of a heart depolarization being undetected. With a small detection margin, no major variation in the heart signal is needed for the duration to be shorter than the detection time. With a large detection margin, transient, long-duration interference with an adequate signal slope, could be interpreted as depolarizations.

Thus, detection conditions, i.e., slope and duration, can be programmable. This also increases the possibility of adapting each detector to the morphology of individual heart signals. In principle, this also makes it possible for the detector to sense other signal components in the heart's electrical signals, such s the T wave. The only requirement is that the slope and duration jointly constitute conditions sufficient for identification of the predetermined signal component in the heart's electrical signal.

In an embodiment of the detector in accordance with the invention the regulatory circuit includes a further operational amplifier, connected to the output terminal of the previously-discussed operational amplifier, at least one resistor, connected between the additional amplifier's output terminal and the first-identified operational amplifier's input terminal, and at least one capacitor, one pole of which is connected to the first-discussed operational amplifier's input terminal and to the further operational amplifier's output terminal. The capacitor's second pole can be connected to a reference potential or to the electrode system.

Alternatively, the detector can be devised so the regulatory circuit comprises a transconductance amplifier, connected between the operational amplifier's output terminal and input terminal, and a capacitor, connected between the operational amplifier's input terminal and the electrode system.

DESCRIPTION OF THE DRAWINGS

FIG. 1 is a schematic illustration of a pacemaker, embodying a detector constructed in accordance with the principles of the present invention, connected in vivo to a heart.

FIG. 2 is a circuit diagram for a first embodiment of a detector constructed in accordance with the principles of the present invention.

FIG. 3 is a circuit diagram for a second embodiment of a detector constructed in accordance with the principles of the present invention.

FIG. 4 is a circuit diagram for a third embodiment of a detector constructed in accordance with the principles of the present invention.

DESCRIPTION OF THE PREFERRED EMBODIMENTS

An implantable pacemaker 2 connected to a heart 4 is schematically shown in FIG. 1. The pacemaker 2 is connected to the heart 4 by an electrode system including a tip electrode 6, a first electrode conductor 8, a ring electrode 10, a second electrode conductor 12 and an indifferent electrode 14. The indifferent electrode 14 is located on the enclosure (can) of the pacemaker 2, but may alternatively comprise the entire enclosure or may be placed alongside the pacemaker 2. The pacemaker can sense heart depolarizations and stimulate the heart 4 when necessary.

In order to sense heart depolarizations, the pacemaker 2 includes a detector as a part of the circuitry contained in its enclosure. The circuit diagram for a detector 16 in a first embodiment of the invention is shown in FIG. 2. Recording of the heart signals is symbolically indicated with a signal source 18, i.e., the heart. The heart signals are sent to the positive input terminal of a first operational amplifier 20. The output signal from the first operational amplifier 20 is sent to the positive input terminal of a second operational amplifier 22. The second operational amplifier 22 is feedback coupled via a resistor 24 to the negative input terminal of the first operational amplifier 20. A capacitor 26 is also connected to the negative input terminal of the first operational amplifier 20. When a voltage signal arrives from the signal source 18 (the heart), the first operational amplifier 20 emits an output signal. This output signal is fed back via the second operational amplifier 22, and a current is generated which charges the capacitor 26. Charging of the capacitor 26 causes the signal gradient between the positive and the negative input terminals of the first operational amplifier 20 to become zero, and the output signal from the first operational amplifier 20 therefore also becomes zero. This balancing of the input signal to the first operational amplifier 20 works well as long as the second operational amplifier 22 is able to supply an output voltage enabling the capacitor 26 to charge sufficiently. Since the battery voltage powering the pacemaker drops as the battery discharges, output voltage from the second operational amplifier 22 drops. This can be remedied by connecting a compensating circuit to the second operational amplifier 22 in order to keep its output voltage constant when battery voltage drops. Alternatively, the resistor 24 can be variable. The resistance of the resistor 24 could then change when battery voltage drops so the peak current to the capacitor remains constant. The resistor 24 and the capacitor 26 are selected to damp all input signals whose signal slope is too flat. When a signal with a sufficiently steep slope arrives at the input terminal of the first operational amplifier 20, the second operational amplifier 22 is no longer able to charge the capacitor 26 fast enough to follow the input signal and damp it down to zero. The first operational amplifier 20 will then supply a peak output signal, either maximally positive or maximally negative. This output signal is sent to a first comparator 28, which compares the output signal to a positive limit voltage U+, and to a second comparator 30 which compares the output signal to a negative limit voltage U−. The limit voltages U+ and U− are selected so they are close to the maximal output signal swing of the first operational amplifier 20. If the input signal has a sufficiently steep positive slope, the first comparator 28 generates an output signal which is sent to a time integrator 32. The duration of the output signal from the first comparator 28 is set in the time integrator 32. If the time integral satisfies a time condition, i.e., a detection time, a heart depolarization is deemed to be present, and an output signal is generated at the output terminal 34 of the time integrator 32. In the corresponding manner, a negative slope at the input terminal of the first operational amplifier 20 will cause the second comparator 30 to generate an output signal which, in turn, is sent to the time integrator 32 in which the duration of the output signal from the second comparator is set in the corresponding way as for the output signal from the first comparator 28. Integration only until the time condition for an approved detection has been satisfied is sufficient. If integration is performed in order to set the total duration of the output signal from the comparators 28 and 30, the detection margin can be set, i.e., the difference between total duration and detection time expressed as a percent of total duration. Assuming that a detection margin should neither be too large nor too small, the detector 16 can be devised to automatically calculate the detection margin at regular intervals and change the detection time accordingly.

A control input terminal 36 has been identified for the time integrator 32, and selective determination of whether positive slopes and/or negative slopes are to be analyzed can be performed via this input terminal. In addition, the time integrator 32 can be devised so the detection time can be changed by, e.g., a physician. An automatic function for changing detection time can thereby be made selectable for the physician, and the use of such a function can be respectively adapted to the patients in whom the pacemaker containing the detector 16 is to be implanted. A control line 38 has also been indicated with a dashed line from the time integrator 32 to the resistor 24. When the resistor 24 is a variable resistor, the time integrator 32 can change the resistance of the resistor 24 via this control line 38, thereby changing the steepness of the regulated signal slope required to cause a peak output signal to be generated from the first operational amplifier 20. If the resistor 24 is a fixed value resistor (i.e., no control line 38 is present) the regulated signal slope is thus set at a predetermined steepness.

All the components in the detector 16 can be arrayed on a microchip, and this has been designated by a boundary line 40 between the detector 16 and external parts (the electrode system and the heart in this instance). Miniaturization of the detector 16 can therefore be maximized. An electricity saving and, in particular space saving detector is thus obtained.

FIG. 3 shows a second embodiment with a detector 42. As in the previous embodiment, the heart signals from a signal source 44, which is the heart, are illustrated. The input signals to the detector 42 are sent via a first capacitor 46 to the positive input terminal of a first operational amplifier 48 and via a second capacitor 50 to the negative input terminal of the first operational amplifier 48. A first resistor 52 is also connected to the negative input terminal. The first capacitor 46 is used to perform the same function as the capacitor 26 in FIG. 2. The second capacitor 50 and the first resistor 52 are used for removing DC signals. The time constant for this RC link can therefore be relatively large, e.g., 1 s. Capacitive coupling of the signal source 44 to the detector 42 makes the detector 42 particularly suitable for an electrode system employing a bipolar lead.

As in the previous embodiment, the output signal from the first operational amplifier 48 is sent to a second operational amplifier 54. In this instance, the output signal is sent to the negative input terminal of the second operational amplifier 54. The output signal from the second operational amplifier 54 can be sent through one or a plurality of switches 56A–D to four resistors 58A–D. The resistors 58A–D have appropriately different resistances. For example, 80 Mohms could be used for resistor 58A, 40 Mohms for resistor 58B, 20 Mohms for resistor 58C and 10 Mohms for resistor 58D. In this way, current is regulated for charging the capacitor 46 in order to quench signal variations across the input terminal of the first operational amplifier 48. One or more of the switches 56A–D can be activated to vary current to the first capacitor 46. In the corresponding way as for the detector 16 in FIG. 2, an input signal with a sufficiently steep positive or negative slope will cause generation of a peak output signal from the first operational amplifier 48. Since subsequent signal conditioning does not differ from the conditioning with the detector 16 in FIG. 2, the same designations have been used for subsequent signal components, i.e., the first comparator 28, the second comparator 30 and the time integrator 32. When a detection is approved, a detection signal is emitted from the signal output terminal 34. The time integrator 32 can be controlled via a control input terminal 36 and can even regulate the regulated signal slope for signals to be allowed to pass the first operational amplifier 48 by controlling the switches 56A–D and, accordingly, controlling the peak current to the first capacitor 46. Automatic regulation of detection time in the time integrator 32 is possible even in this instance. This can be accomplished in the same way as described above for FIG. 1.

The boundary line 60 indicates that all the components in the detector 42 can advantageously be arrayed on a microchip, making the detector 42 very current- and space-saving.

A third embodiment is shown in FIG. 4 in which a detector 62 receives signals from a signal source 64 at the positive input terminal of an operational amplifier 68 via a first capacitor 66. A first resistor 70 is connected to the negative input terminal of the operational amplifier. A second resistor 72 is feedback connected in parallel with a second capacitor 74 between the output terminal of the operational amplifier 68 and its negative input terminal. This is to filter out high-frequency signal components. A transconductance amplifier 76 is feedback connected to the positive input terminal of the operational amplifier 68. Here, the output terminal of the operational amplifier 68 is connected to the negative input terminal of the transconductance amplifier 76. The transconductance amplifier 76 generates a current when a voltage arrives at the input terminal. The current charges the first capacitor 66 and accordingly damps input signals to the operational amplifier 68 in such a way that the voltage gradient between the input terminals of the operational amplifier 68 is minimized. The peak current the transconductance amplifier 76 is able to generate then limits the signal slope which can be damped out. Steep positive and negative slopes will, as described above for the detector 16 and the detector 42, cause a peak output signal from the operational amplifier 68. The subsequent signal processing and subsequent components of the detector 62 are also identical to the aforesaid embodiments. Positive slopes are compared to a positive limit voltage U+ in the first comparator 28, and negative flanks are compared to a negative limit voltage U− in the second comparator 30. The time integrator 32 sets the duration of output signals from the comparators 28 and 30 and generates an output signal when a detection occurs. The time integrator 32 can be controlled via the control input terminal 36 and automatically regulates the detection time and peak current from the transconductance amplifier 76. The latter value is regulated by changing the resistance of a variable resistor 78 which is connected to the transconductance amplifier 76 and which regulates its peak output current.

All components for the detector 62 can advantageously be arrayed on a microchip. The boundary line 80 designates the border between the detector 62 and external components, such as the electrode system.

The three described embodiments can be combined in different ways to achieve other versions of detectors based on the invention. For example, the switches 56A–D and the resistors 58A–D in FIG. 2 could easily replace the variable resistor 24 in FIG. 1. The capacitor 50 and the resistor 52 in FIG. 2 can have the same function in all the described embodiments of the detector, as the coupling of the resistors 70 and 72 and the capacitor 74 in FIG. 3.

In addition, electrical signals from the heart can advantageously be preamplified before being sent to the detector. This preamplification can also be implemented in the detector itself.

The detector can be advantageously utilized in all types of devices in which heart depolarizations are to be detected, implantable devices such as pacemakers and defibrillators in particular.

Although modifications and changes may be suggested by those skilled in the art, it is the intention of the inventor to embody within the patent warranted hereon all changes and modifications as reasonably and properly come within the scope of his contribution to the art.

I claim as my invention:

1. A detector for detecting depolarizations in a heart, comprising:

means for sensing a cardiac signal from a heart, said cardiac signal having a slope;

an operational amplifier having a first input connected to said means for sensing, and supplied with said cardiac signals, a second input, and an output;

regulatory means, feedback coupled between said second input and said output of said operational amplifier, for setting a regulated slope, said first and second inputs thereby exhibiting a voltage difference thereacross, and for minimizing said voltage difference across said first and second inputs of said operational amplifier as long as said cardiac signal has a slope which is flatter than said regulated slope and thereby causing said operational amplifier to generate substantially no signal at its output, and for causing said operational amplifier to be driven to generate a maximum peak output signal at its output as long as said cardiac signal has a slope steeper than said regulated slope; and timer means, connected to said output of said operational amplifier, for starting and timing a time interval when said operational amplifier generates said maximum peak output signal and for generating a detection signal indicating the occurrence of a depolarization of said heart if said time interval exceeds a predetermined detection time.

2. A detector apparatus as claimed in claim 1 wherein said timer means comprises:

a first comparator means for comparing said output signal from said operational amplifier to a positive limit voltage and for generating a first comparator means output signal as long as said output signal from said operational amplifier is higher than said positive limit voltage; and second comparator means for comparing the output signal from said operational amplifier to a negative voltage limit and for generating a second comparator means output signal as long as said output signal from said operational amplifier is lower than said negative limit voltage.

3. A detector as claimed in claim 2 wherein said timer means further comprises integrator means for respectively determining a duration of said first comparator means output signal and a duration of said second comparator means output signal, and for comparing said duration with said detection time.

4. A detector as claimed in claim 3 wherein said regulatory means comprises means for varying said regulated slope, said means for varying said regulated slope having an input connected to an output of said integrator and varying said regulated slope dependent on the duration of said first comparator means output signal or said second comparator means output signal.

5. A detector as claimed in claim 4 wherein said integrator comprises an integrator wherein said detection time is programmable, and wherein said integrator comprises means for automatically varying said detection time dependent on the duration of said first comparator means output signal or said second comparator means output signal for maintaining a detection margin.

6. A detector as claimed in claim 3 wherein said integrator comprises an integrator wherein said detection time is programmable, and wherein said integrator comprises means for automatically varying said detection time dependent on the duration of said first comparator means output signal or said second comparator means output signal for maintaining a detection margin.

7. A detector as claimed in claim 1 wherein said regulatory means comprises:

a further operational amplifier having an input connected to said output of said operational amplifier, and having an output, a resistor connected between said output of said further operational amplifier and said second input of said operational amplifier, and a capacitor having a terminal connected to said second input of said operational amplifier and to said output of said further operational amplifier.

8. A detector as claimed in claim 6 wherein said capacitor has a further terminal connected to a reference potential.

9. A detector as claimed in claim 6 wherein said capacitor has a further terminal connected to said means for sensing a cardiac signal.

10. A detector as claimed in claim 1 wherein said regulatory means comprises:

a transconductance amplifier having an input connected to said output of said operational amplifier, and having an output; and a capacitor connected between said second input of said operational amplifier and said means for sensing a cardiac signal.

* * * * *